United States Patent [19]

Williams et al.

[11] Patent Number: 5,318,534

[45] Date of Patent: Jun. 7, 1994

[54] SYRINGE FOR BALLOON CATHETERIZATION

[75] Inventors: Eli Williams, North Salt Lake; Evan Call, Bountiful, both of Utah

[73] Assignee: Professional Medical, Inc., N. Salt Lake, Utah

[21] Appl. No.: 30,567

[22] Filed: Mar. 12, 1993

[51] Int. Cl.⁵ .......................................... A61M 29/00
[52] U.S. Cl. ...................................... 604/97; 604/99
[58] Field of Search .................. 604/97, 98, 99, 100, 604/211, 214, 188, 146

[56] References Cited

U.S. PATENT DOCUMENTS

| | | | |
|---|---|---|---|
| 4,370,982 | 2/1983 | Reilly | 604/99 |
| 4,583,974 | 4/1986 | Kokernak | 604/211 |
| 4,651,738 | 3/1987 | Demer et al. | 606/102 |
| 4,723,938 | 2/1988 | Goodin et al. | 604/99 |
| 4,740,203 | 4/1988 | Hoskins et al. | 604/97 |
| 4,758,223 | 7/1988 | Rydell | 604/98 |
| 4,832,692 | 5/1989 | Box et al. | 604/211 |
| 4,919,121 | 4/1990 | Rydell et al. | 604/99 |
| 4,940,459 | 7/1990 | Noce | 604/99 |
| 5,019,041 | 5/1991 | Robinson et al. | 604/211 |
| 5,047,015 | 9/1991 | Foote et al. | 604/98 |
| 5,084,060 | 1/1992 | Freund et al. | 604/100 |
| 5,137,514 | 8/1992 | Ryan | 604/99 |
| 5,147,300 | 9/1992 | Robinson et al. | 604/97 |
| 5,168,757 | 12/1992 | Rabenau et al. | 604/99 |
| 5,209,732 | 5/1993 | Lampropoulos et al. | 604/98 |

*Primary Examiner*—C. Fred Rosenbaum
*Assistant Examiner*—N. Kent Gring
*Attorney, Agent, or Firm*—Trask, Britt & Rossa

[57] ABSTRACT

A unique syringe useful in the inflation and rapid deflation of a balloon used in balloon catheterization (transluminal angioplasty) procedures is disclosed. The syringe has a uniquely actuated thread engaging block which is engaged and disengaged by a rotary cam member interacting with the thread-engaging block. The thread engaging block engages a threaded piston rod which is attached to the piston within the barrel of a balloon catheter syringe. A rotary cam member engages the block so as to exert a positive force on the block, either moving the block into a thread engaging position or moving into a thread disengaging position. The unique syringe may also contain a piston face which is segmented so that a portion of the piston face is separately actuatable in order to introduce a minor increase in pressure while the main piston member remains in a stationary position.

3 Claims, 8 Drawing Sheets

SYRINGE FOR BALLOON CATHETERIZATION

BACKGROUND OF THE INVENTION

1. Field of the Invention

The instant invention relates to syringes for inflating a balloon in a balloon catheterization device and to the systems and methods associated with balloon catheterization (transluminal angioplasty procedures).

2. State of the Art

Numerous syringes for balloon catheterization are extant in the art. A representative sampling of such syringes are disclosed in the following patents: U.S. Pat. No. 5,047,015 to Foote et al.; U.S. Pat. No. 4,832,692 to Box et al.; U.S. Pat. No. 4,651,738 to Demer et al.; U.S. Pat. No. 4,940,459 to Noce et a).; U.S. Pat. No. 4,583,974 to Kokernak and U.S. Pat. No. 5,084,060 to Freund et al. An exhaustive list of additional patents exists in the references cited portion of the Foote et al patent.

Devices disclosed in the above-identified patents are quite similar in structure; having a barrel and plunger or piston configured so that the piston may be screwed into the barrel in small increments to increase pressure on fluid within the barrel. Ultimately, the pressurized fluid flow into the balloon in a slow, controlled manner to inflate the balloon. Generally, all syringes disclosed in the above-identified patents have a quick release mechanism whereby the threaded engagement between threaded piston rod and the internal threads within the syringe body are quickly disconnected, allowing the piston rod and piston to slide freely within the device and be quickly retracted to reduce rapidly fluid pressure within the balloon.

Various techniques and means are employed to bring about the disengagement between the threaded portions of the piston rod and the syringe housing. In the Foote et al. patent the threads on the piston rod are permitted to retract when a trigger mechanism is pulled to cause the piston rod threads to slide along an inclined plane to remove them from contract with the threads of the syringe body. In Box et al. a lever on top of the syringe is pushed towards the syringe by the palm of the hand to press against a threaded member to push that threaded member away from contact with the threads of the piston rod.

In both the Box et al. and Foote et al. devices a spring member is used to maintain the two threaded members in contact with one another. In the Kokernak device, a locking mechanism rotates and is locked in place by spring loaded balls which fit into detents. Thus, in all three patents, springs are relied upon to hold the threads in an engagement position.

Although these devices may work well, there is the risk that a spring will fatigue and allow the threads to disengage at an inopportune or critical moment. Furthermore, in the manufacture of the device some machined piece of metal or plastic might become lodged in the spring cavity thereby preventing the spring from being depressed, thereby restraining the piston from disengagement. Either of these situations could result in adverse consequences to a catheterization patient.

SUMMARY OF THE INVENTION

The instant invention involves a syringe for balloon catheterization in which the threads (splines) contained within the body of the syringe on a splined block and the threads on the piston rod connected to the piston are engaged and disengaged manually by positive action without the use of any spring biases. Further, the syringe is constructed so that it may be held in one hand, for example, the left hand and the threaded engagement means operated by one thumb upon a handle connected to a screw element (rotary cam) which retracts and engages a threaded block structured to engage the threads of the piston rod. Thus, the syringe may be held in the left hand and, with the right hand, the piston rod turned which screws the rod into the body of the syringe thereby advancing the piston within the barrel chamber to create fluid pressure within the balloon attached to plastic tubing connected to the discharge end of the barrel.

In order to disengage the threaded piston rod, the thumb of the left hand, for example, may be placed upon the wing-like handle of the retraction/insertion member (rotary cam) whereby the handle is moved (rotated) from an engagement position to a disengagement position which rotates the rotary cam to retract the splined block. Both the retraction and engagement action of the splined block is controlled by a positive positioning action that is either a clockwise or a counterclockwise rotation of the rotary cam.

An advantage of the device of the instant invention is that the splined block may be retracted and left in a retracted position. There is no spring bias upon the block which would force it back into a engagement position as in other devices. Furthermore, in retracting the splined block there is no spring bias which must be overcome by force applied by the operator to cause such disengagement. The only force that must be overcome is the force which exists on the splined block because of pressure reaction of the pressurized fluid upon the piston.

The device of the instant invention comprises a body which supports a cylindrical barrel at its distal end. The barrel, at its proximal end, has a wide mouth opening which permits the insertion of a piston member within the barrel. The piston member fits tightly within the barrel and generally is sealed to the barrel by o-rings or by a rubbery, membrane-like cap on the end of the piston whereby the rubbery cap has a diameter slightly greater than the piston so that it seals the piston to the interior wall of the barrel. A threaded piston rod, which preferably is of a large diameter equal to or only slightly smaller than the diameter of the piston, is attached to or integral with the proximal end of the piston. The piston rod is threaded and extends outward of the proximal end of the syringe body.

A splined block is contained within the syringe body and is oriented substantially perpendicularly to the longitudinal axis of the piston rod. The splined block is attached to an insertion/retraction member (rotary cam) which is a screw-like member which fits within the splined block and is also oriented substantially perpendicularly to the longitudinal axis of the piston rod.

The retraction/insertion member protrudes through the top wall of the syringe body (it is preferably the top wall although it could be either side wall or the bottom wall) with a wing-like handle attached radially to the insertion/retraction member (rotary cam) so that it is substantially parallel to the longitudinal axis of the piston rod and is in a position relative to the syringe body so that the wing-like handle may be manipulated easily with the thumb of the left hand while the left hand is gripping the syringe body from underneath, that is the palm of the left hand would be in contact with the underside of the syringe body. Another particularly good feature of this invention is that it may be readily operated by either right or left handed people with or without a minor change in the orientation of the winged-handle.

Further description of the invention may be facilitated by reference to the following drawings.

DETAILED DESCRIPTION OF THE INVENTION

Figure 1:
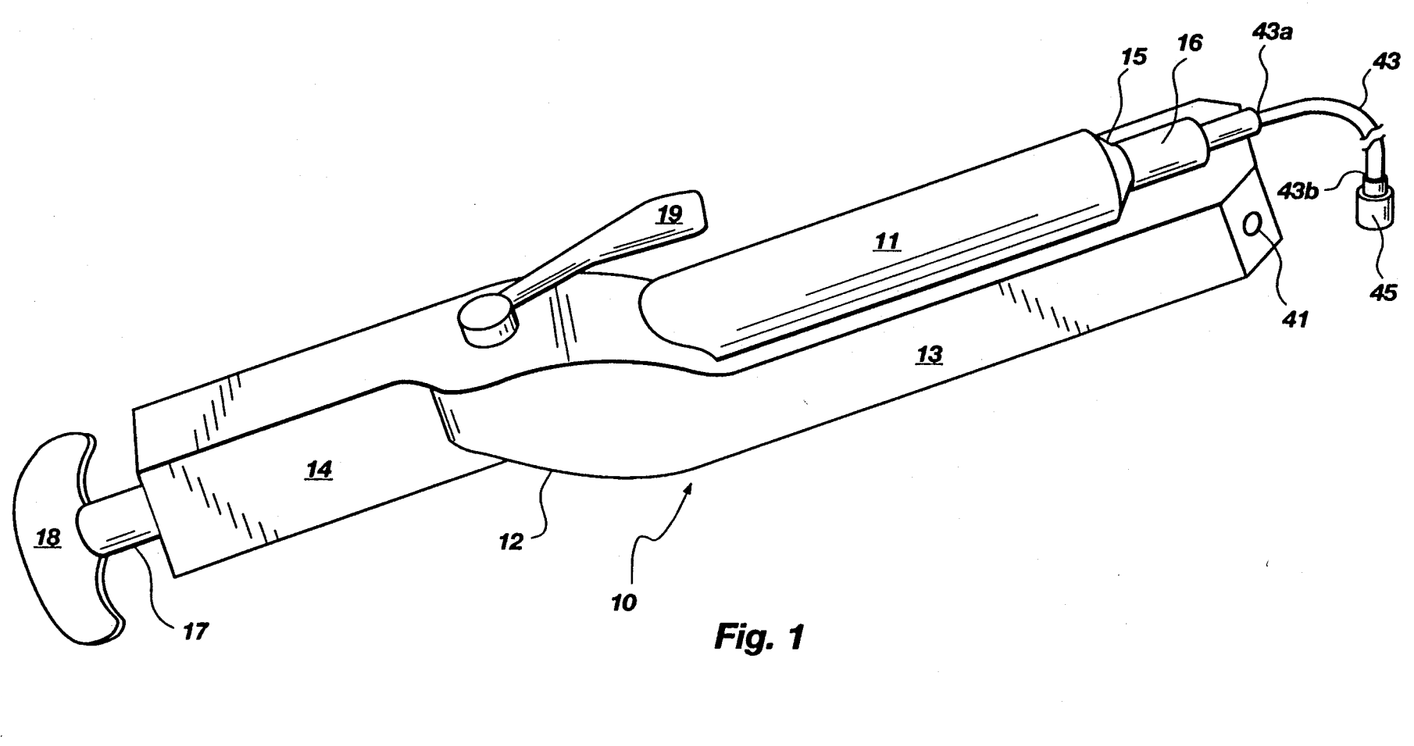
FIG. 1 is a perspective view of the balloon catheter syringe of the instant invention.

A preferred embodiment of the invention is illustrated in FIG. 1 which is a perspective view of a balloon catheter syringe 10 having a cylindrical barrel 11 supported by an elongated syringe body 12 which has a barrel supporting portion 13 and a hand-grip portion 14. The discharge end of the barrel has a cone-shaped end 15 which is integral with a nozzle 16. The nozzle may connect to a flexible tubing which forms part of the tubing that is inserted into a vein or artery. In a preferred construction, a flexible tubing member 43 is connected to the nozzle 16 at the first end 43a and is fitted on its opposing end 43b with a Luer connector 45. The luer connector in turn may be fitted with a conventional catheter (not shown). At the proximal end of the syringe body, a piston rod 17 projects towards the person using the device and is capped with a handle 18.

On the top surface of the syringe body is a wing-like handle 19 which can be rotated from a first position which is an engagement position which causes engagement between the threads of the piston rod and the splined block, said handle 19 being rotatable to a second position which is a disengagement position for the splined block.

Figure 2:
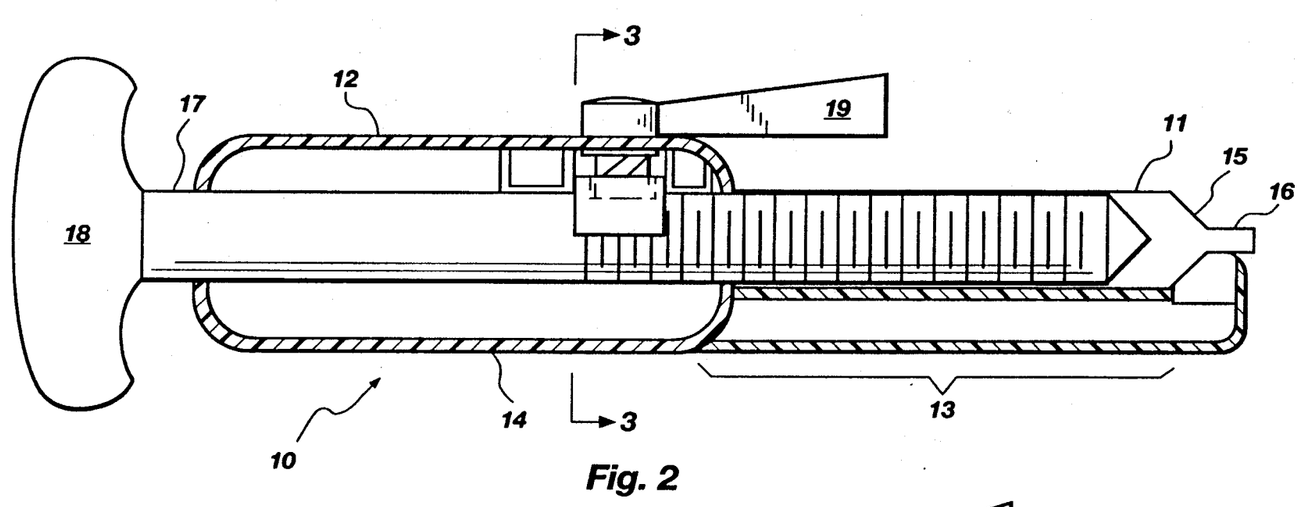
FIG. 2 is an elevational, partial, sectional view of the syringe of FIG. 1 along section lines 2—2.

FIG. 2 is an elevational partial sectional view of the balloon catheter syringe illustrating the interaction if the splined moveable block and the piston rod/plunger. As illustrated to be seen that the piston rod is the same diameter as the plunger and as will be noted in other embodiments the piston rod may be hollow to accommodate another interior rod. The piston portion of the piston rod plunger unit fits within the cylindrical barrel of the unit. The barrel is supported by the syringe body and has a proximal open end with a supporting flange around its said open being the same diameter as the interior of the barrel to accommodate the entrance of the piston into the barrel.

Figure 3:
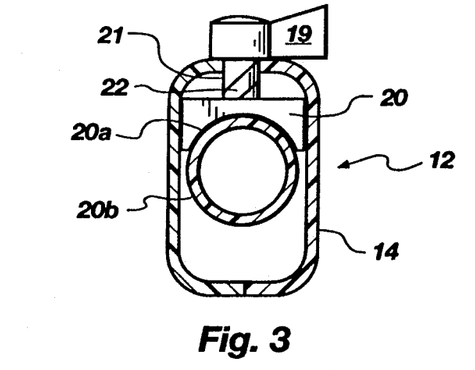
FIG. 3 is a sectional view of the syringe of FIG. 1 along section lines 3—3.
Figure 4:
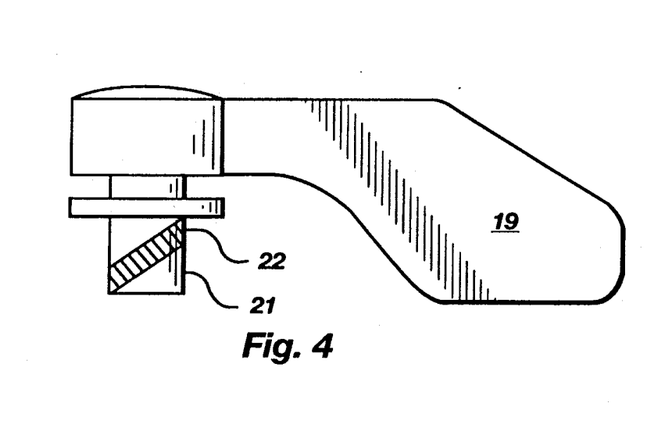
FIG. 4 is an elevational view of the actuator mechanism of the syringe of FIG. 1.

FIGS. 3 and 4 illustrate the quick release mechanism of the instant invention wherein a winged handle 19 is attached to a cylindrical pin-like element 21 which has a cam race 22 within it, wherein the cam race 22 interacts with a protrusion (not shown) within the threaded block 20 so that rotation of the pin-like member causes the splined block 20 to move upward or downward depending upon the rotation of the wing-like handle 19 attached to the pin-like, cam member 21.

Figure 15:
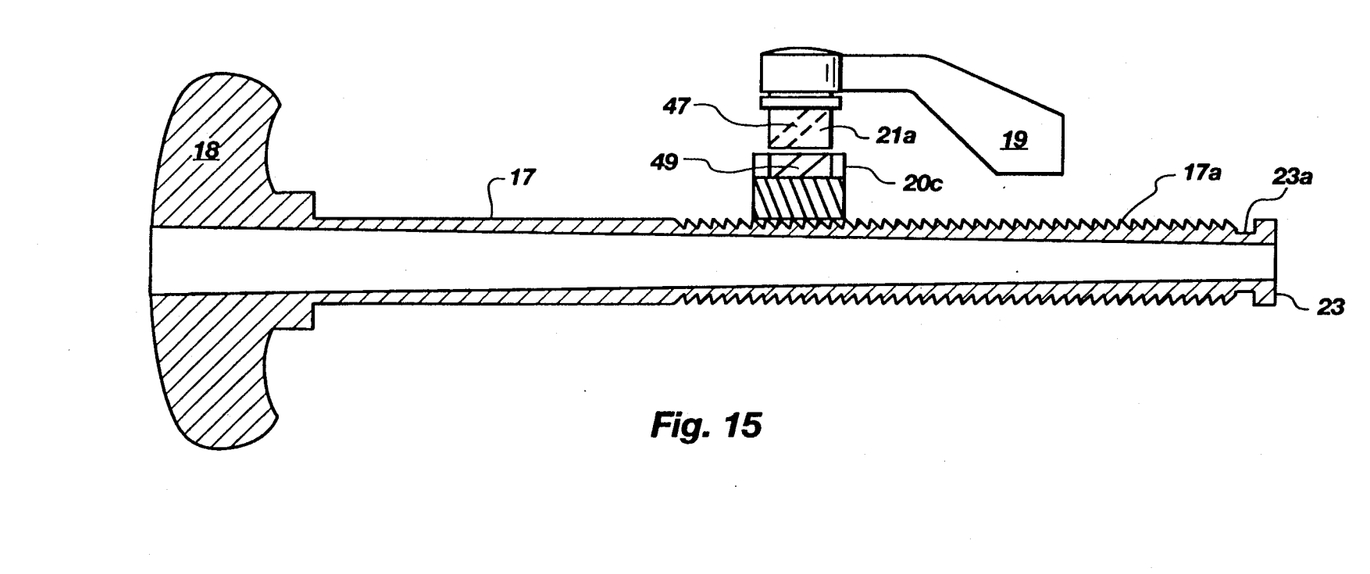
FIG. 15 is a cross-sectional side view of an alternative construction of a threaded piston rod of the invention.

In an alternative embodiment, a raised spiral cam surface 47 may be defined on the pin-like member 21a to interact with a spiral race 49 defined in the inner surface wall of the block 20c which receives the pin-like member 21a.

Preferably, the pitch of the cam threads is about two threads per inch, which causes about an one-eighth inch displacement of the block for each 90° of rotation of the pin.

The threaded block 20 has a partial-cylindrical surface 20a which is threaded to interact with the threads on the threaded piston rod 17. The threads on surface 20a are the only threads associated with the internal base 20b of the syringe body. Thus, when the threaded block 20 is in an upward position, the threads on the piston rod 17 are disengaged, allowing the piston rod to move freely to the rear when fluid pressure within the barrel pushes on the piston. Surface 20a is preferably less than a semi-cylindrical surface so that less upward movement is required to cause disengagement between the threaded piston rod and the threads on surface 20a.

The term "splines" has also been used herein to describe the threads on surface 20a.

The pin-like member 21 may have conventional threads on its surface so that it "screws" into threaded block 20 to move it upwards. Also, the pin-like member 21 may be secured to the block 20 in a rotatable manner with its threads interacting with threads in the top surface of the syringe to cause the pin-like member to rise when rotated in one direction and to carry said block 20 with it, thereby raising the block to cause it to disengage from threads on the piston rod. Rotation of the pin-like member in the other direction would cause the block to lower and to engage the threads of the piston rod.

Figure 5:
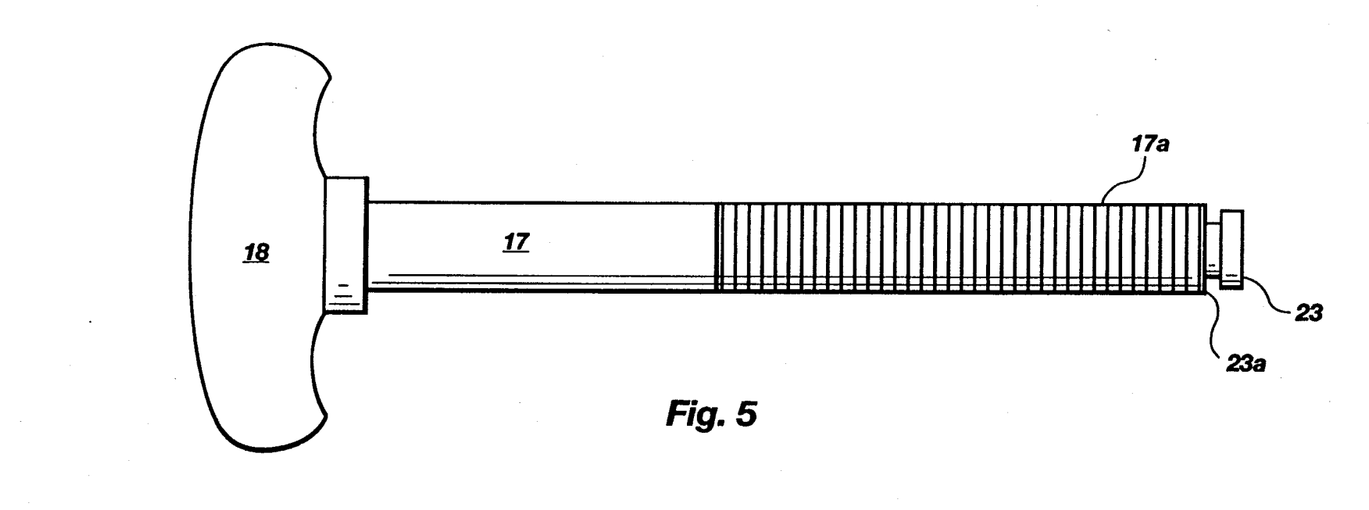
FIG. 5 is an elevational view of the piston rod of the syringe of FIG. 1.
Figure 6:
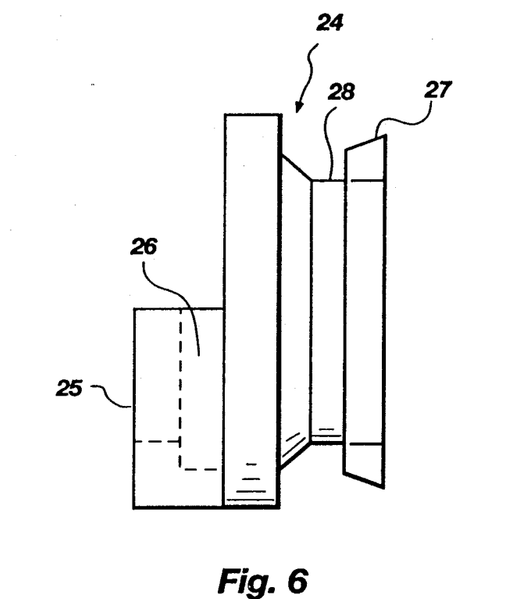
FIG. 6 is a side, elevational view of a plunger tip which interacts with the piston i.e. plunger, end of the piston rod of FIG. 5.

The piston element of the invention is illustrated in more detail in FIG. 5 wherein a disc-like element 23 is attached to the distal end, that is the pressure end, of the piston 17a. The smaller diameter disc 23 enables a plunger-tip to be secured to the end of the plunger. The disc 23 is preferably integral with the piston and spaced slightly apart from the piston and leg groove 23a. The plunger tip is illustrated in FIG. 6. The length of the piston rod is about 10 to 15 times the diameter of the piston. The piston rod handle 18 may be any general shape. It can be a knob although a flat handle-like member is generally preferred.

Figure 7:
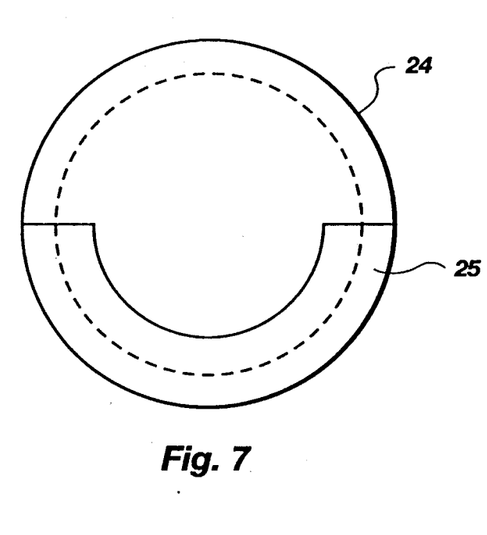
FIG. 7 is an elevational, rear view of the plunger tip of FIG. 5.

The plunger tip 24 is illustrated in FIGS. 6 and 7 and is designed with a semi-circular cup 25 to fit partially over the disk-like member 23 on the tip of the plunger. However, in the instant embodiment it is a separate element whereby the semi-circular cup 25 has a semi-circular cavity 26 which mates with the disk 23 on the tip of the plunger to hold the plunger tip 24 in place when the elements are within the barrel of the syringe. The plunger tip 24 permits the piston 17a to rotate without causing the tip 24 to rotate. The plunger tip 24 further has the larger, disk-like element 27 and a groove 28 behind it to accommodate a flexible rubbery diaphragm which is slightly larger than the plunger tip and is illustrated in FIG. 8.

Figure 8:
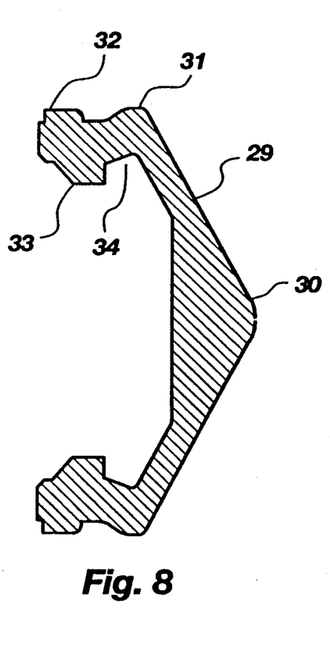
FIG. 8 is a side, elevational, sectional view of a circular, rubbery end cap which co-acts with the plunger tip of FIG. 7.

The diaphragm-like member 29 illustrated in FIG. 8 forms an end cap for the piston. It is a rubbery material and is of sufficient diameter that it seals the end of the plunger within the barrel so as the plunger moves forward into the liquid within the barrel, the liquid does not seep past the seal formed by the end cap. Thus, pressure can be exerted upon the liquid within the barrel. Other arrangements of constructing a plunger, of course, could be utilized. For example, the piston could have 0-rings about the cylindrical circumference of the piston to form a seal. 0-rings have been used in other syringe plungers to effectuate a seal between the piston and the internal barrel wall.

The end cap 29 has a front face 30 which is circular and continuous. Around its circumference it has a laterally protruding ring 31 which fits very tightly within the barrel of the device to form a pressure tight seal. A secondary seal is formed by seal ring 32 which is to the rear of seal ring 31. An internal collar 33, i.e. a circular internal ridge is adapted to fit within groove 28 of the plunger tip (See FIGS. 6, 7, 11 and 12) to secure the end cap 29 to the plunger tip. A circular groove 34 in the end cap mates with the rim of disk 27 of the plunger tip 24 to hold the end cap 29 securely to the plunger tip.

Figure 9:
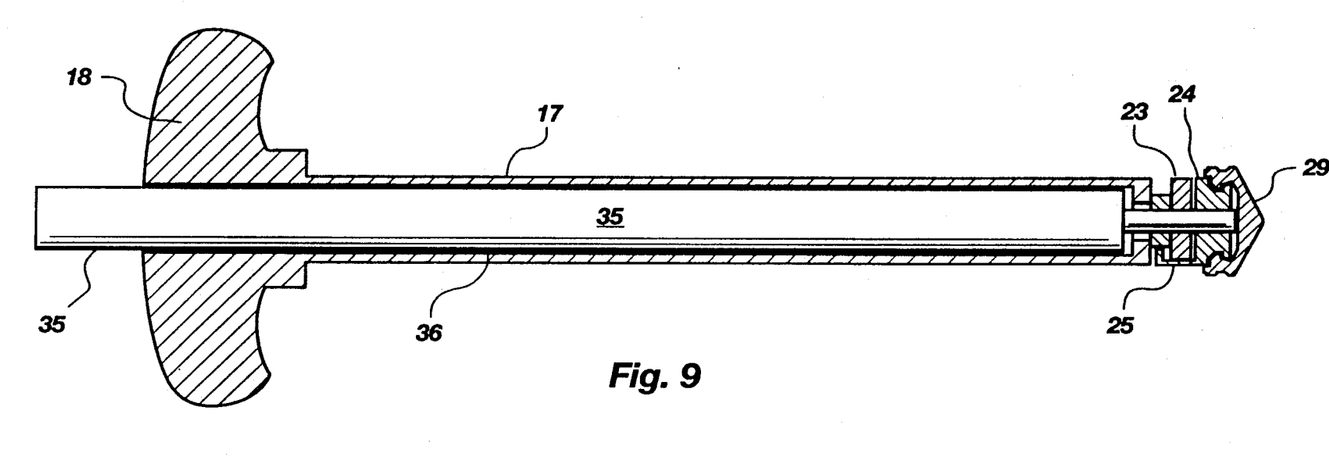
FIG. 9 is an elevational, sectional view of a syringe of the type illustrated in FIG. I with a dual piston comprising a main piston and a secondary piston.

FIG. 9 illustrates a syringe having a pair of concentric plungers with a small plunger (piston) rod 35 concentrically enclosed within the outer (main) piston rod 17. A bore 36 through the center of the piston rod/piston and plunger tip allows the small diameter, straight secondary plunger rod to slide within the outer plunger to contact the internal facial surface of rubbery end cap 29. The rear or proximal end of the secondary plunger protrudes from the rear of handle 18. An operator of the syringe can reciprocate secondary piston rod to distend the face of end cap 29 to increase the pressure in the barrel of the syringe and ultimately to increase the pressure within the balloon.

Figure 11:
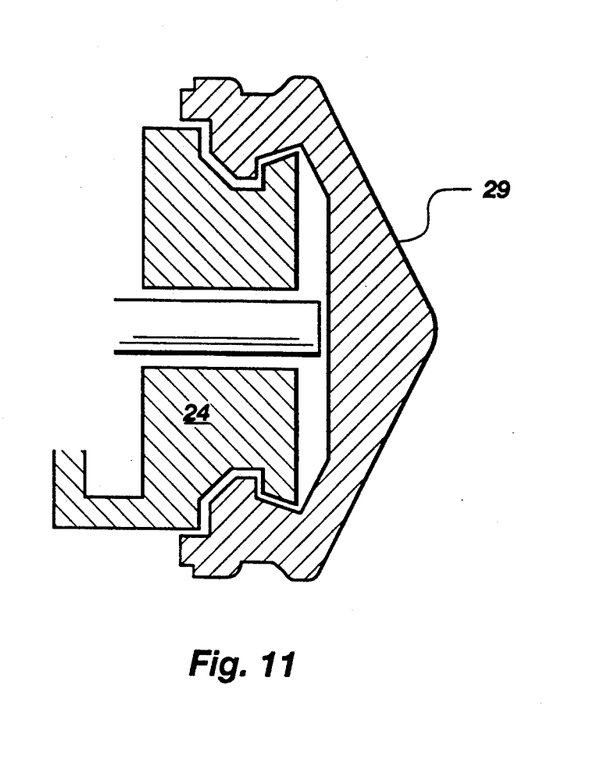
FIG. 11 is an enlarged view of the end cap portion of the syringe illustrated in FIG. 9 in a normal condition.
Figure 12:
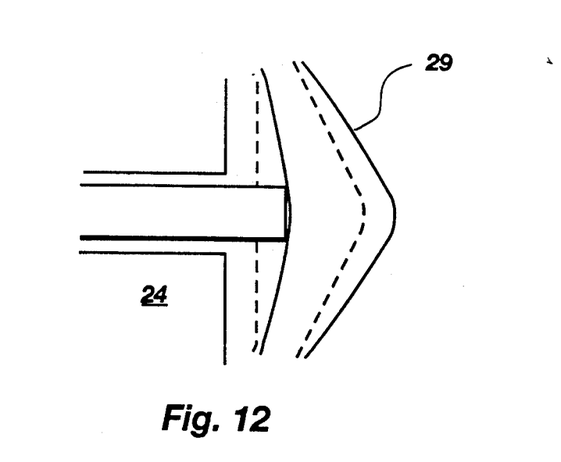
FIG. 12 is an enlarged view of the end cap portion of the syringe illustrated in FIG. 9 with the secondary plunger in a forward position, distending the rubbery end cap.

The normal position of the secondary piston rod is illustrated in FIG. 11. The distal end 35a of the piston rod presses through the plunger tip 24 to rest against the internal face of end cap 29. When the secondary plunger rod 35 is pushed forward it distends end cap 29 as illustrated in FIG. 12. The distal end 35a may, as illustrated, be slightly smaller in diameter than the diameter of secondary rod 35 so that it more easily passes through smaller openings in disk 23 and plunger tip 24.

Figure 10:
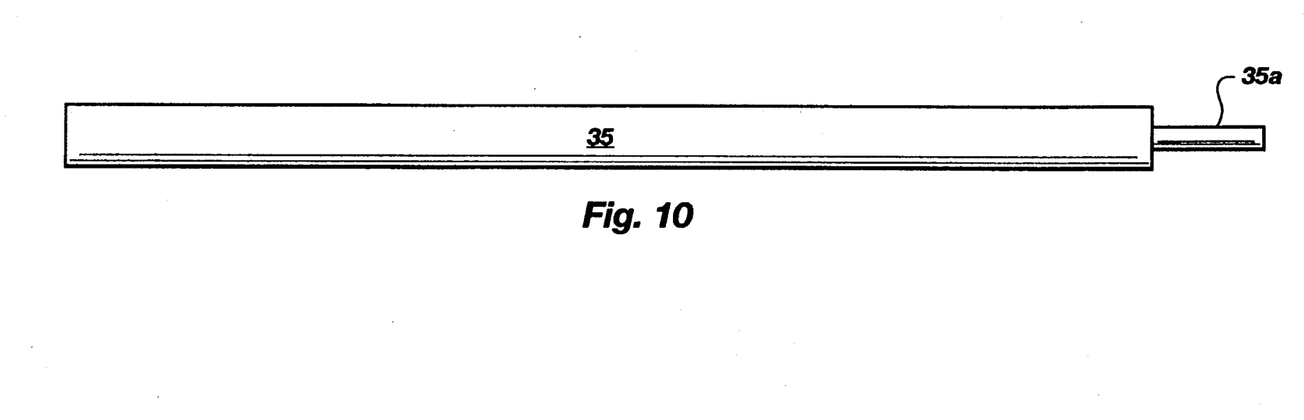
FIG. 10 is an elevational view of a secondary piston.

A particular advantage of the diaphragm-like end cap 29 is that an internal or secondary plunger 35 can be concentrically fixed within the main plunger rod 17. This is illustrated in FIG. 9. Also FIG. 10 illustrates the secondary plunger rod which is contained concentrically within the main piston rod 17.

The purpose of the second plunger rod 35 is that when the main plunger 17 has been threaded into the barrel a certain distance to achieve a certain desired pressure within the balloon of the balloon catheter, then by reciprocating the secondary plunger, the diaphragm is distended like end cap 29 (see FIG. 12) into the liquid and a pulsating pressure may be applied to the balloon and thus effectuate a better compression of the plaque within a particular artery or vessel. (The dotted lines in FIG. 12 shows the normal position for the face of end cap 29. The solid lines show the distend position.)

Some technicians are currently achieving this pulsating pressure effect by rotating the main plunger rapidly to increase and decrease the pressure. However, rotation of the main plunger may have certain risks in that it is perhaps easy to apply too much pressure and it can also be tiring to the wrist. In the instant invention, the device is constructed so that when one is holding the main plunger, one can press on the secondary plunger at its proximal end with a thumb or with the palm of the hand to slightly move the diaphragm at the distal end of the secondary plunger to induce an increase in pressure of perhaps 10 to 40 percent. The maximum pressure increase can be designed into the unit by predetermining the diameter of the secondary plunger and predetermining the length of the secondary plunger at its proximal end which projects from the handle so as to control the amount of distortion of the diaphragm into the catheter fluid.

Figure 13:
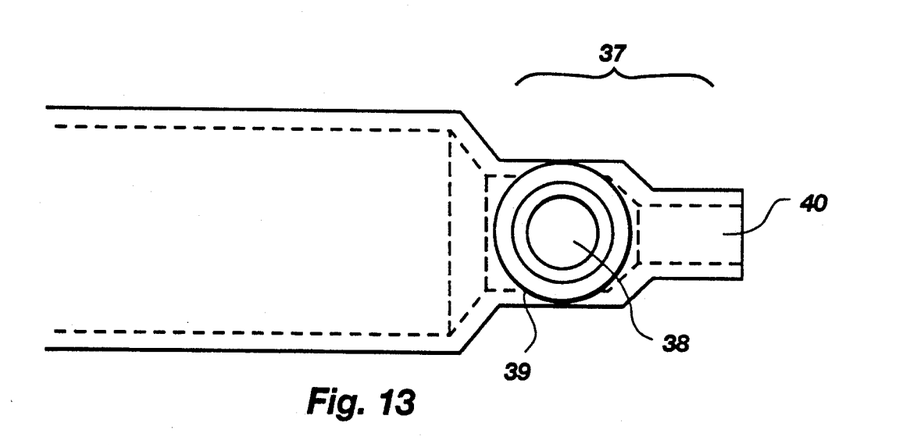
FIG. 13 is a plan view of the discharge nozzle of the syringe of FIG. 1 having an adaptation to accommodate a pressure transducer.
Figure 14:
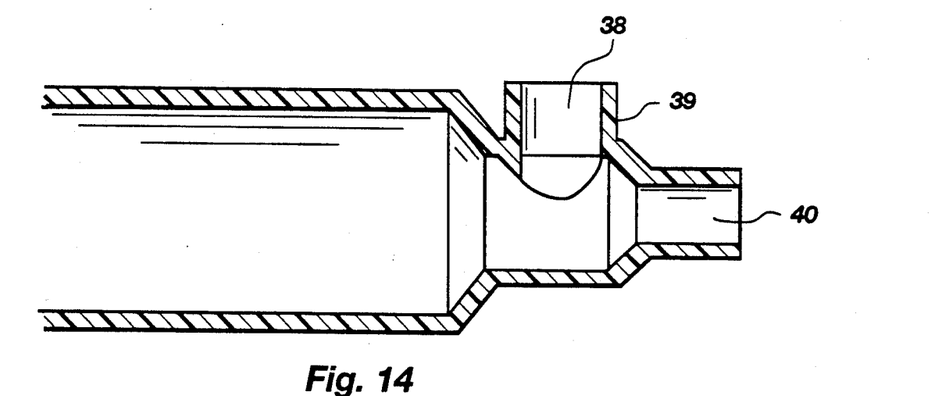
FIG. 14 is an elevational view of the syringe nozzle of FIG. 13.

FIGS. 13 and 14 illustrate another unique feature of the instant invention. The nozzle structure 37 forward of the barrel 11 is modified to be able to hold a pressure transducer (not shown). The pressure transducer fits within receptacle 38 formed by the cylindrical walls 39. The transducer is in contact with fluid inside the nozzle and is capable of accurately determining fluid pressure. Receptacle 38 communicates with flow channel 40 within nozzle structure 37.

In the instant invention, as can be seen in FIG. 1, the syringe body 14 has a barrel supporting section 13 which, if desired, may contain electronic components suitable for being connected to the transducer for converting the analog electrical output of the transducer to digital outputs. Also, the digital signals may be electronically processed to form infrared information signals capable of being transmitted from the syringe to a remote receiver display, as more fully described in co-pending applications of these inventors. The IR transmitting elements, e.g. diodes 41 (See FIG. 1) may be located on the syringe body and are preferably located at the front of the syringe body on opposite sides of the body so that the wide beam IR signal from each of a pair of IR transmitting elements covers the total region forward, above and below the syringe so that a strong IR information securing signal will be received regardless of the orientation of the syringe.

What is claimed is:

1. A balloon catheter syringe having a syringe body and a barrel having a plunger tightly fitting within said barrel, a threaded plunger rod fitted to said plunger and a moveable thread engaging member interacting with said threaded plunger; the improvement comprising:

a cylindrical cam member rotatably attached to said syringe body rotatable about its longitudinal axis having means to interact with said thread engaging member to engage and disengage said thread engaging member from the threads of said threaded plunger rod upon rotation of said cam member in opposite directions whereby said thread engaging member moves topwards or away from said threaded plunger rod upon rotation of said cam in different directions.

2. A balloon catheter syringe having a barrel, a displaceable piston a threaded piston rod attached at its distal end to said displaceable piston said piston comprising:

a syringe body for supporting said barrel;

a smooth bore contained within said body, said bore sized to receive said piston rod;

a splined block contained within said syringe body, said block displaceable transversely to said piston rod to occupy two positions, a first position being a piston rod thread engaging position and a second disengaging position;

a splined block actuator mechanism having a threaded screw member rotatably attached to said body with the threaded position of said screw engaging said splined block whereupon rotation of said screw around its central longitudinal axis in one direction causes said splined block to engage said piston rod and rotation of said screw in an opposite direction disengages said splined block from the threads of said piston rod.

3. A balloon catheter syringe having a syringe body comprising:

a barrel with an inner bore of substantially uniform diameter supported by said syringe body;

a resilient piston member sized to making sealing contact with said inner bore of said barrel, said piston having a continuous face for contacting a fluid within said barrel and a rear side structured to engage a piston rod;

an outer piston rod reciprocally moveable within said inner bore of said barrel, said outer piston rod joined to said piston, said outer piston rod having an internal bore structured to receive a second, smaller piston rod;

a second piston rod slidingly engaging said internal bore of said outer piston rod, said second piston rod having a distal end structured to engage the backside of said resilient piston member and capable of causing said piston member face to flex when said inner piston rod is moved against or removed from contacting the backside of said piston member; and means for restraining length of travel of said inner piston rod within said outer piston rod.

* * * * *